US012385830B2

(12) United States Patent
Hamilton et al.

(10) Patent No.: US 12,385,830 B2
(45) Date of Patent: Aug. 12, 2025

(54) TEMPERATURE COMPENSATION SYSTEM AND METHOD FOR NIR SAMPLE ON BALER

(71) Applicant: AGCO Corporation, Duluth, GA (US)

(72) Inventors: Kevin J. Hamilton, Newton, KS (US); Patrick Kendrick, Hesston, KS (US)

(73) Assignee: AGCO Corporation, Duluth, GA (US)

( * ) Notice: Subject to any disclaimer, the term of this patent is extended or adjusted under 35 U.S.C. 154(b) by 652 days.

(21) Appl. No.: 17/758,032

(22) PCT Filed: Dec. 9, 2020

(86) PCT No.: PCT/IB2020/061692
§ 371 (c)(1),
(2) Date: Jun. 27, 2022

(87) PCT Pub. No.: WO2021/137064
PCT Pub. Date: Jul. 8, 2021

(65) Prior Publication Data
US 2023/0341322 A1 Oct. 26, 2023

Related U.S. Application Data

(60) Provisional application No. 63/119,617, filed on Nov. 30, 2020, provisional application No. 62/954,776, filed on Dec. 30, 2019.

(51) Int. Cl.
G01N 21/3563 (2014.01)
A01F 15/04 (2006.01)
(Continued)

(52) U.S. Cl.
CPC ......... G01N 21/3563 (2013.01); A01F 15/04 (2013.01); A01F 15/08 (2013.01);
(Continued)

(58) Field of Classification Search
CPC ............. G01N 21/3563; G01N 21/359; G01N 33/245; G01N 33/246; G01N 35/00693;
(Continued)

(56) References Cited

U.S. PATENT DOCUMENTS 6,559,655 B1 * 5/2003 Rosenthal .......... G01N 21/3563
250/252.1
11,991,956 B2 * 5/2024 Hamilton ................. G01N 1/04
(Continued)

FOREIGN PATENT DOCUMENTS

EP 3 162 189 A2 5/2017
WO 2019/050412 A1 3/2019

OTHER PUBLICATIONS

European Patent Office, International Search Report related to International Patent Application No. PCT/IB2020/061692, mail date Feb. 15, 2021.

Primary Examiner — Ryan D Walsh

(57) ABSTRACT

A baler includes a near-infrared testing system configured to receive near-infrared radiation reflected by plant material in a bale and to analyze the near-infrared radiation and generate evaluation data reflecting one or more properties of the plant material. The near-infrared testing system is calibrated using a calibration sample at a calibration temperature. A temperature sensor measures a sample temperature of a crop sample of the plant material. A computer receives and combines the evaluation data of the plant material and a temperature-difference offset based on the difference in the sample temperature of the crop sample and the calibration temperature to produce overall temperature-compensated evaluation data reflecting one or more overall property values for the bale, and assign the overall temperature-compensated evaluation data to the at least one bale of the plurality of bales.

6 Claims, 14 Drawing Sheets

(51) Int. Cl.
*A01F 15/08* (2006.01)
*G01N 1/28* (2006.01)
*G01N 21/359* (2014.01)
*G01N 21/84* (2006.01)
*G01N 33/24* (2006.01)
*G01N 35/00* (2006.01)
*G06Q 10/0639* (2023.01)
*G06Q 50/02* (2024.01)

(52) U.S. Cl.
CPC ......... *G01N 21/359* (2013.01); *G01N 33/245* (2024.05); *G01N 33/246* (2013.01); *G01N 35/00693* (2013.01); *G06Q 10/06395* (2013.01); *G06Q 50/02* (2013.01); *G01N 2001/2866* (2013.01); *G01N 2021/8466* (2013.01)

(58) Field of Classification Search
CPC .... G01N 2001/2866; G01N 2021/8466; A01F 15/04; A01F 15/08; G06Q 10/06395; G06Q 50/02
See application file for complete search history.

(56) References Cited

U.S. PATENT DOCUMENTS

| | | |
|---|---|---|
| 2006/0283166 A1* | 12/2006 | Schlesser ............ A01F 15/0816 56/341 |
| 2009/0217827 A1 | 9/2009 | Duenwald et al. |
| 2017/0013772 A1 | 1/2017 | Kirk et al. |
| 2017/0118918 A1* | 5/2017 | Chaney ............... A01F 15/0883 |
| 2018/0332773 A1* | 11/2018 | Roberts ............. G01N 21/3563 |
| 2022/0346323 A1* | 11/2022 | Hamilton ........... A01F 15/0825 |

\* cited by examiner

TEMPERATURE COMPENSATION SYSTEM AND METHOD FOR NIR SAMPLE ON BALER

CROSS REFERENCE TO RELATED APPLICATION

This application claims the benefit of U.S. Provisional Application No. 63/119,617, filed Nov. 30, 2020 and U.S. Provisional Application No. 62/954,776, filed Dec. 30, 2019, which are hereby incorporated by reference in their entirety.

BACKGROUND OF THE INVENTION

Field

The present invention relates to systems and methods for evaluating materials in bales, and more particularly, embodiments concern a system and method for adjusting for crop temperature to achieve a more accurate weighted average quality value for the overall bale.

Description of Related Art

A swather, or windrower, is an agricultural machine configured to cut plant material growing in a field and arrange the cut portions in windrows on the field in a swath to dry. An example swather is the Massey Ferguson WR9980 self-propelled windrower. At the time of swathing, the plant material may have approximately eighty-five percent moisture content. At approximately thirty percent moisture content, a rake machine may merge and turn the windrows to facilitate further drying in preparation for baling. It is common to package such plant material into bales for subsequent sale, transport, or other use. A baler is an agricultural machine configured to collect the windrowed and dried plant material, compress, shape, and secure it in the form of a bale. An example baler is the Massey Ferguson 2270XD square baler. At the time of baling, the plant material may have approximately twelve to eighteen percent moisture content.

It is known to test a sample of the plant material in order to determine properties (e.g., protein content, fiber content, nitrate content, ash content, moisture content, nitrate content, ash content) that are relevant to its sale or use value. Typically, once a number of bales have been created, a core sample is taken from one of the bales and sent to a third-party laboratory for, e.g., near-infrared (NIR) testing or wet chemistry testing and analysis to determine these properties. In an NIR testing system, light having wavelengths between, e.g., 780 nm and 2500 nm, is emitted by the instrument and at least a portion is reflected by the plant material; received, filtered, and converted to a voltage or current; and then analyzed to determine the properties of the plant material.

The accuracy of NIR testing is highly dependent on the calibration methods applied to the spectra, and calibration methods and results are typically very well documented for NIR testing systems. Different calibration models used by different labs can be built using different wet chemistry testing procedures and results from one lab might vary as much as 30% to 50% compared to another lab which significantly effects the value and end use of the plant material. Another problem with this process is the long time required for the sample to reach the laboratory, the testing and analysis to be performed, and the results to be returned.

Another problem is that the sample from one or even several bales from a field may not be representative of the quality of the many other bales from the same field. In some cases, hundreds of tons of plant material are presented by a mere fifty grams of it in the laboratory. Additionally, traceability of where bales of hay come from is an important piece of information, and where the hay came from can be misrepresented either by error or by intent. Another problem is to accurately represent the bale, the sample needs to be cored, stored and shipped appropriately. Failure to properly take care of the sample can cause substantial changes, which in turn can affect the value of the hay.

It is increasingly desirable to test bales on site, but doing so requires associating calibration and filtering information with each bale and otherwise meeting the specific requirements of individual customers. For example, many larger customers, such as large dairy operations or other operations engaged in state, national, or international sales, require that testing be conducted by specific laboratories using specific processes in order to deliver a standardized product, which is not satisfied by generic calibration methods and results.

Further, an NIR sensor component of the NIR testing system is typically mounted either in a feeding mechanism or in a compression chamber of the baler. Due to the nature of the baling operation, the amount of time the NIR sensor is exposed to a given portion of the plant material will vary with such factors as the mass of the crop; the speed of the baler; encountering areas of the field previously baled (headlands); and the settings of the baler, such as the speed of a power take-off, the load, and a trip pressure of a stuffer. Similarly, part of the bale may be scanned as the bale exits the compression chamber, which results in a much lower sampling rate for that portion of the bale. As the aggregated plant material in an individual bale may not be homogenous in its properties, property values may be assigned to individual bales that do not reflect the actual overall quality of those bales.

Additionally, the NIR sensor component of the NIR testing system is typically positioned in the compression chamber and scans the finished bale so as to minimize effects of the baling process. However, the condition of the sample taken from the portion of the bale that the NIR sensors scan may be quite different from the conditions of the sample that was used to calibrate the NIR sensing system, which can produce unreliable results due to differing conditions.

This background discussion is intended to provide information related to the present invention which is not necessarily prior art.

SUMMARY

Embodiments address the above-identified and other problems and limitation in the prior art by providing a system and method for evaluating individual subunits of material incorporated into a bale and, based thereon, assigning a weighted average quality value to the overall bale.

In one embodiment, a system incorporated into a baler machine is configured to receive a plant material, and to aggregate, compress, shape, and secure the plant material into a plurality of bales. The system includes a near-infrared testing system configured to receive near-infrared radiation reflected by the plant material in at least one bale of the plurality of bales and to analyze the near-infrared radiation and generate evaluation data reflecting one or more properties of the plant material in the at least one bale, wherein the near-infrared testing system is calibrated using a calibration sample at a calibration temperature. The system includes a temperature sensor configured to measure a sample temperature of a crop sample of the plant material. The system includes a computer configured to receive and combine the evaluation data of the plant material and a temperature-difference offset based on a temperature difference value to account for difference in the sample temperature of the crop sample and the calibration temperature to produce overall temperature-compensated evaluation data reflecting one or more overall property values for the bale, and assign the overall temperature-compensated evaluation data to the at least one bale of the plurality of bales.

Another embodiment is directed to a method for sampling agricultural crop material formed into a bale. The method includes calibrating a near-infrared testing system using a calibration sample having a calibration sample temperature. A baler receives, aggregates, shapes and secures plant material into a bale. The method includes preparing a crop sample of the plant material of the bale and measuring the temperature of the crop sample with a temperature sensor. The temperature of the crop sample is compared with the calibration sample temperature at which the near-infrared testing system was calibrated. A computer receives and combines the evaluation data of the plant material and adding a temperature difference offset to account for difference in the temperature of the crop sample and the calibration sample temperature to produce overall temperature-compensated evaluation data reflecting one or more overall property values for the bale, and assigns the overall evaluation data to the bale.

This summary is not intended to identify essential features of the present invention, and is not intended to be used to limit the scope of the claims. These and other aspects of the present invention are described below in greater detail.

DRAWINGS

Embodiments of the present invention are described in detail below with reference to the attached drawing figures, wherein.

The figures are not intended to limit the present invention to the specific embodiments they depict. The drawings are not necessarily to scale.

DETAILED DESCRIPTION

The following detailed description of embodiments of the invention references the accompanying figures. The embodiments are intended to describe aspects of the invention in sufficient detail to enable those with ordinary skill in the art to practice the invention. Other embodiments may be utilized and changes may be made without departing from the scope of the claims. The following description is, therefore, not limiting. The scope of the present invention is defined only by the appended claims, along with the full scope of equivalents to which such claims are entitled.

In this description, references to "one embodiment," "an embodiment," or "embodiments" mean that the feature or features referred to are included in at least one embodiment of the invention. Separate references to "one embodiment," "an embodiment," or "embodiments" in this description do not necessarily refer to the same embodiment and are not mutually exclusive unless so stated. Specifically, a feature, component, action, step, etc. described in one embodiment may also be included in other embodiments, but is not necessarily included. Thus, particular implementations of the present invention can include a variety of combinations and/or integrations of the embodiments described herein.

Figure 1:
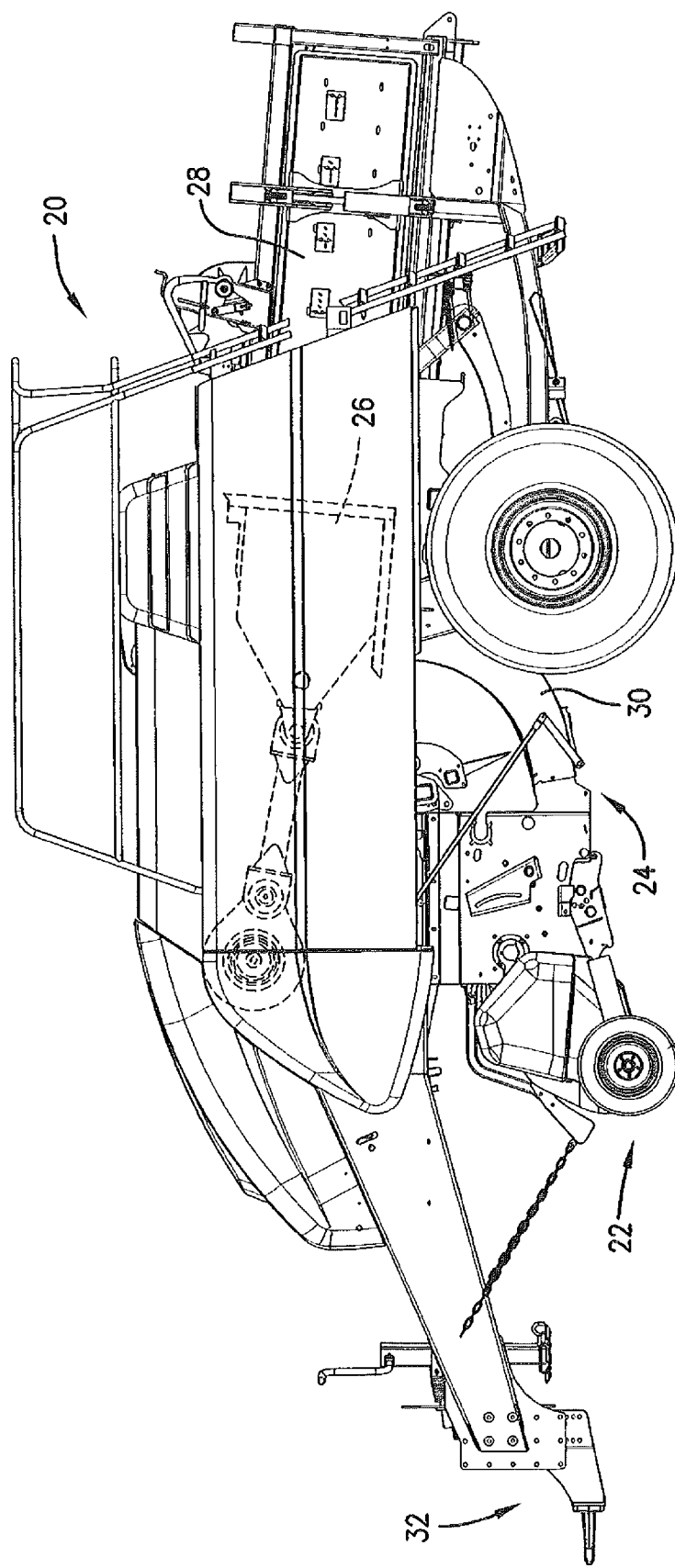
FIG. 1 is a side elevation view of an example baler machine configured to receive loose plant material and compress, shape, and secure the material into a bale.

Referring to FIG. 1, an example baler machine 20 is shown into which embodiments of the present invention may be incorporated. Although the example baler 20 is a towed square baler, it will be appreciated that embodiments of the present invention may be incorporated into other types of balers (e.g., self-propelled, round) with few or no changes. Broadly, the baler 20 may be configured to move over a field and collect previously cut plant material and to compress, shape, and secure the collected plant material into a plurality of bales. The baler 20 may generally include a pickup assembly 22, a stuffer chute assembly 24, a reciprocating plunger 26, and a baling (or compression) chamber 28.

The pickup assembly 22 may be configured to collect the cut plant material from the field. In one implementation, the pickup assembly 22 may include a pair of ground wheels 30 that support the pickup assembly 22 as the baler 20 moves over the field. The stuffer chute assembly 24 may be configured to direct the collected plant material into position for incorporation into a bale. In one implementation, the stuffer chute assembly 24 may include a charge-forming duct 30 extending from an inlet opening adjacent to the pickup assembly 22 to an outlet opening into the baling chamber 28. The reciprocating plunger 26 may be configured to compress the plant material from the charge-forming duct 30 into a growing bale. In one implementation, the plunger 26 may be configured to reciprocate within the baling chamber 28 in repeating compression and retraction strokes across the outlet opening of the charge-forming duct 30. As the plunger 26 retracts, the outlet opening is uncovered and an additional flake, charge, or other subunit of plant material enters the baling chamber 28, and as the plunger 26 contracts the outlet opening is covered and the additional subunit of plant material is compressed into the growing bale. The baling chamber 28 may be configured to shape the growing bale and secure the compressed plant material in the individual bale. The finished bale may be ejected rearwardly to land on the field behind the baler for subsequent collection. Additionally, the baler 20 may be hitched to a towing vehicle (not shown) by a tongue 32, and power for operating the various mechanisms (e.g., the reciprocating plunger 26) of the baler 20 may be supplied by a power take-off of the towing vehicle.

Some embodiments may create and physically associate an identifying element containing a unique identifier with an individual bale of plant material, wherein the identifying element contains or the unique identifier can be used to find both calibration information for an NIR testing system used to evaluate one or more properties of interest of the particular plant material into the bale and the evaluation information which may be provided in terms of values for the one or more properties of interest. By defining and physically associating the calibration information with the unique bale identifier, a customer for, inspector of, or other entity interested in the feedstuffs or other plant-based biomaterial incorporated into the bale can quickly and easily view the values for the one or more properties of interest for the individual bale, and can understand and be able to refute or accept these values based on how the information was processed for, e.g., a particular region or customer.

In one implementation, the identifying element may be a radio-frequency identification (RFID) tag, including a microchip and an antenna, embedded or otherwise incorporated into a twine, strap, or other binding material securing the plant material into the bale. In another implementation the identifying element may take the form of a flat tag attached to the twine, strap, or other binding material. In another implementation, the identifying element may take the form of a bar code or similar technology.

In one implementation, the identifying element may contain only the unique identifier, and the unique identifier can be used to look-up or otherwise find the calibration information and the evaluation information in one or more databases. In another implementation, the identifying element may contain the unique identifier and the calibration information and/or the evaluation information. In this implementation, the system may include an electronic transfer mechanism configured to electronically write or otherwise electronically transfer to the identifying element during the process of creating the bale the calibration and/or the evaluation information.

In one implementation, the calibration information may include any one or more of an identification of a technician who calibrated the NIR testing system, a date on which the NIR testing system was calibrated, a date on which the current calibration expires, a treatment and filtering method, a calibration identifier, an intended type of plant material, and an identification of an employer of the technician, which may be AGCO Corporation or another commercial or public entity. Calibration information can be generated in different ways, and in particular, there are different ways to correlate spectral response and calibration. In one implementation, the NIR sensor may be an AGCO sensor and the calibration information may be generated using an AGCO calibration standard, while in another implementation, the NIR sensor may be a non-AGCO sensor and/or the calibration information may be generated using a non-AGCO calibration standard.

In one implementation, the evaluation information may include any one or more of a protein content, a fiber content, a nitrate content, an ash content, a moisture content, a relative feed value (RFV) for the plant material, soluble protein, uNDF, WSC, NSC, Starch, and Nitrates.

Figure 2:
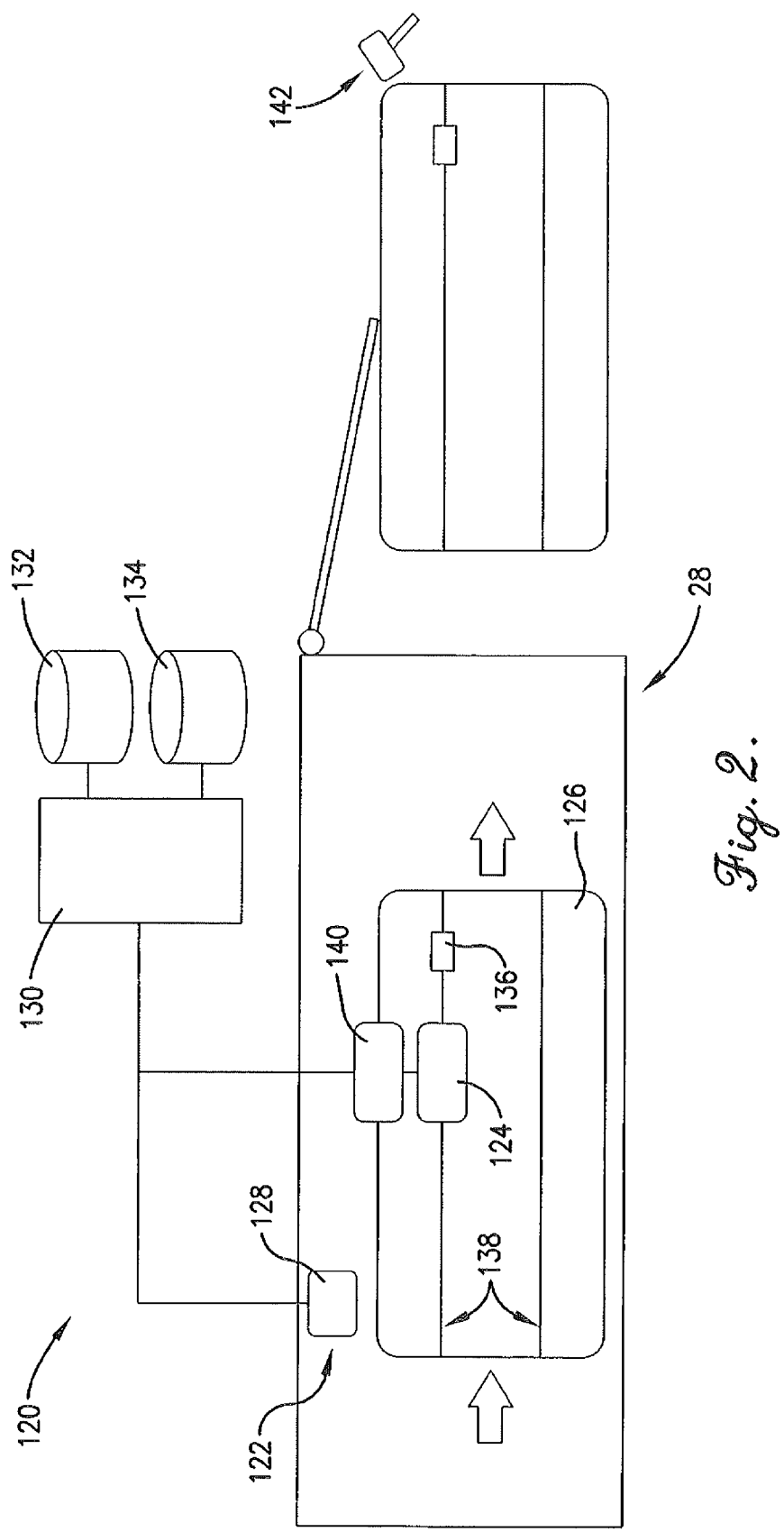
FIG. 2 is a high-level block diagram of an embodiment of a system for creating and physically associating an identifying element with an individual bale of plant material, wherein the identifying element includes a unique identifier and includes or can be used to find calibration and evaluation information.

Referring also to FIG. 2, an embodiment of a system 120 is shown for creating and physically associating an identifying element with an individual bale of plant material, wherein the identifying element includes a unique identifier and includes or can be used to find calibration and evaluation information. The system 120 is shown incorporated into an example operating environment. The system 120 may comprise some or all of the baler machine 20, an NIR testing system 122, and an identifying element securement system 124, which may function in accordance with the method 220 described below. As discussed, the baler machine 20 may be configured to receive plant material and to compress, shape, and secure the plant material into a plurality of bales 126. In one implementation, the baler 20 may be otherwise substantially conventional in design, construction, and operation.

The NIR testing system 122 may be configured to emit near-infrared radiation and receive a reflected response from the plant material in all or some (e.g., one of every five or fewer bales, or one of every ten or fewer bales) of the bales, analyze the near-infrared radiation, and generate evaluation information reflecting one or more properties of the plant material in each analyzed bale, and may be associated with calibration information which is relevant to the accuracy of the evaluation information.

In one implementation, the NIR testing system 122 may include one or more NIR sensors 128 and a computer 130. The NIR sensor 128 may be mounted in or on or otherwise incorporated into the baling chamber 28 or other area of the baler 20, and may be configured to receive, filter, and convert to a voltage or current the near-infrared radiation reflected by the plant material in the bale 126, and transmit the voltage or current to the computer 130. The computer 130 may be located on or remotely from the baler 20, and may be configured to receive the voltage or current transmitted by the NIR sensor 128 and analyze the voltage or current to determine the properties of the plant material and generate the evaluation information reflecting those properties. The computer 130 may then assign a unique identifier to the bale 126, associate the calibration information for the NIR testing system 122 with the unique identifier for the bale 126, and associate the evaluation information for the bale 126 with the unique identifier for the bale 126. In various implementations, the unique identifier may be used to find the calibration information for the NIR testing system 122 in a first database 132, the unique identifier may be used to find the evaluation information in a second database 134, or the calibration and the evaluation information may be stored together in a single database. In another implementation, one or both of the calibration information and the evaluation information may be stored on a physical identifying element (described below) attached to the bale 126 by the identifying element securement system 124.

In one implementation, the calibration information may include one or more of an identification of a technician who calibrated the individual NIR testing system 122, a date on which the NIR testing system 122 was calibrated, a treatment and filtering method, a calibration identifier, an intended type of plant material, and/or an identification of an employer of the technician. In one implementation, the evaluation information may include one or more of a protein content, a fiber content, nitrate content, ash content, a moisture content, and/or a relative feed value for the plant material in the bale 126.

The identifying element securement 124 system may be mounted in or on or otherwise incorporated into the baling chamber 28 of the baler 20, and configured to physically secure to the individual bale 126 a physical identifying element 136 configured to physically associate the unique bale identifier with the bale 126, wherein, as discussed, the unique bale identifier is associated with and may be used to find the calibration information for the NIR testing system 122 and the evaluation information for the plant material in the bale 126.

In one implementation, the physical identifying element 136 may be an RFID tag including an integrated circuit and an antenna embedded or otherwise incorporated into a top, front, or end center portion of a binding material 138 (e.g., twine, strap or similar material) which secures the bale 126. In another implementation, the physical identifying element 136 may take the form of a flat tag similarly attached to the binding material 138. In one implementation, the physical identifying element 136 already has the unique bale identifier stored thereon, and the identifying element securement mechanism 124 need only secure the physical identifying element 136 to the bale 126. In another implementation, the identifying element securement mechanism 124 may include an identifying element writing mechanism 140 configured to electronically write or otherwise transfer the unique bale identifier on the identifying element 136 prior to, simultaneous with, or subsequent to its securement to the bale 126. Further, as discussed, one or both of the calibration and the evaluation information may be stored on a physical identifying element 136, in which case the identifying element writing mechanism 140 may be further configured to electronically write or otherwise transfer one or both of the calibration information and the evaluation information to the physical identifying element 136, such that this information and/or information can be subsequently directly read from the physical identifying element 136 using, e.g., a hand-held reading device 142.

The system 120 may include additional details discussed elsewhere herein, including those discussed below in describing the operating method 220.

Figure 3:
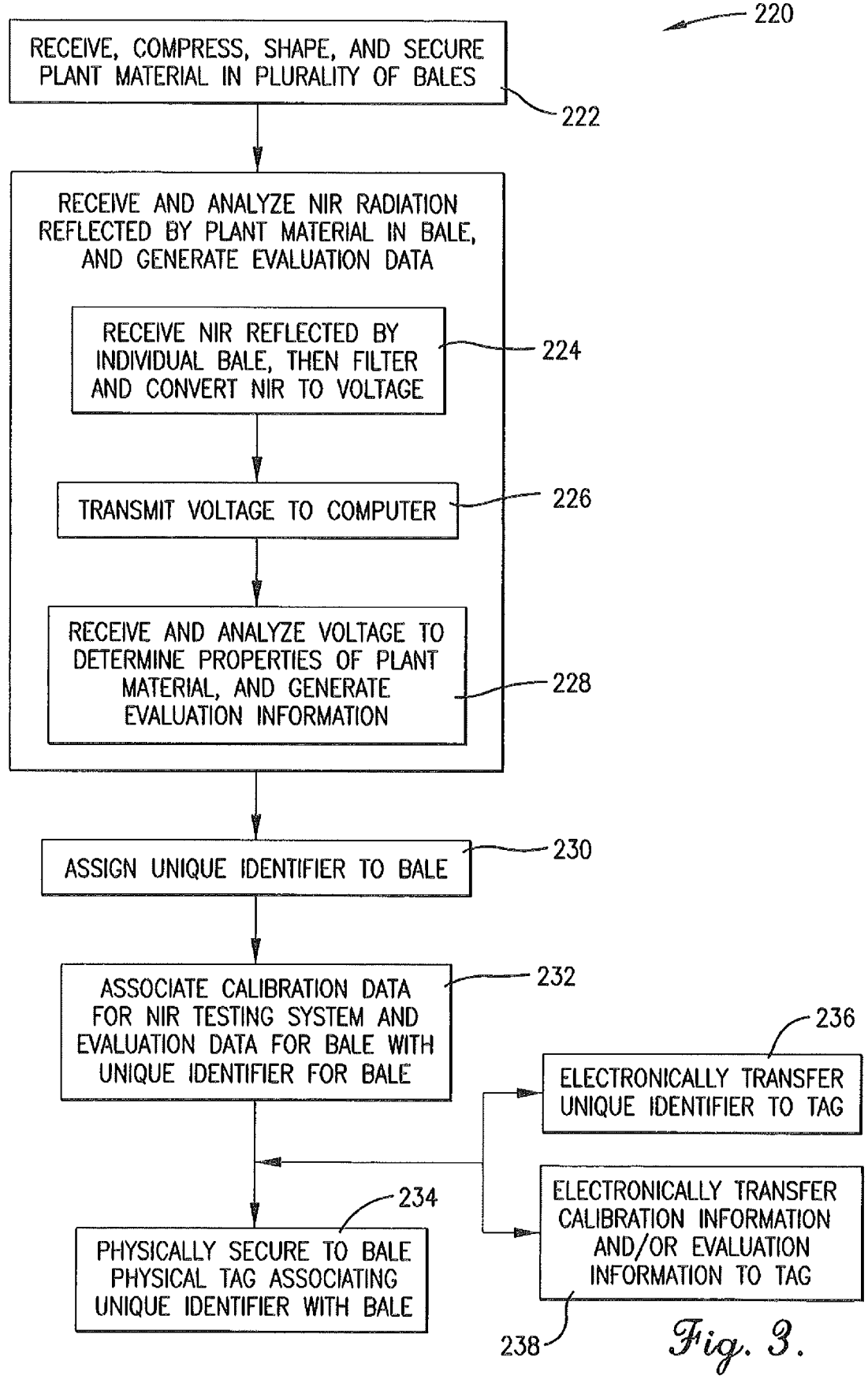
FIG. 3 is a flowchart of steps in an embodiment of a method for creating and physically associating an identifying element with an individual bale of plant material, wherein the identifying element includes a unique identifier and includes or can be used to find calibration and evaluation information.

Referring also to FIG. 3, an embodiment of a method 220 is shown for creating and physically associating an identifying element with an individual bale of plant material, wherein the identifying element includes a unique identifier and includes or can be used to find calibration and evaluation information. The method 220 may refer to an example operating environment. The method 220 may comprise some or all of the following steps, which may be implemented by components of the system 120 described above.

As discussed, plant material may be received and shaped and secured by a baler machine 20 into a plurality of bales 126, as shown in step 222.

Near-infrared radiation emitted by an NIR testing system 122 and reflected by the plant material in the bale 126 may be received, filtered, and converted to a voltage or current by an NIR sensor 128 component of the NIR testing system 122, as shown in step 224, and the voltage or current may be transmitted to a computer 130 component of the NIR testing system 122, as shown in step 226. In various implementations, the NIR sensor 128 may be mounted in or on or otherwise incorporated into the baling chamber 28 or other area of the baler 20, and the computer 130 may be located on or remotely from the baler 20. In various implementations, one of every five or fewer bales may be subject to such testing, or one of every ten or fewer bales may be subject to such testing. The voltage or current transmitted by the NIR sensor 128 may be received and analyzed by the computer 130 to determine the properties of the plant material and generate evaluation information reflecting those properties, as shown in step 228.

A unique identifier may be assigned by the computer 130 to the bale 126, as shown in step 230, and the calibration information for the NIR testing system 122 and the evaluation information for the bale 126 may be associated by the computer 130 with the unique identifier for the bale 126, as shown in step 232. In various implementations, the unique identifier may be used to find the calibration information for the NIR testing system 122 in a first database 132, the unique identifier may be used to find the evaluation information in a second database 134, or the calibration information and the evaluation information may be stored together in a single database. In another implementation, one or both of the calibration information and the evaluation information may be stored on a physical identifying element (described below) attached to the bale 126 by the identifying element securement system 124.

In one implementation, the calibration information may include one or more of an identification of a technician who calibrated the individual NIR testing system 122, a date on which the NIR testing system 122 was calibrated, a treatment and filtering method, a calibration identifier, an intended type of plant material, and/or an identification of an employer of the technician. In one implementation, the evaluation information may include one or more of a protein content, a fiber content, a moisture content, and/or a relative feed value for the plant material in the bale 126.

A physical identifying element 136 physically associating the unique bale identifier with the bale 126 may be physically secured to the individual bale 126 by an identifying element securement system 124, as shown in step 234. The identifying element securement system 124 may be mounted in or on or otherwise incorporated into the baling chamber 28 of the baler 20. In one implementation, the physical identifying element 136 may be a radio-frequency identification tag including an integrated circuit and an antenna embedded or otherwise incorporated into a top, front, or end center portion of a binding material 138 (e.g., twine, strap or similar material) which secures the bale 126. In another implementation, the physical identifying element 136 may take the form of a flat tag similarly attached to the binding material 138. In one implementation, the physical identifying element 136 already has the unique bale identifier stored thereon, and the identifying element securement mechanism 124 need only secure the physical identifying element 136 to the bale 126.

In another implementation, the unique bale identifier may be electronically written or otherwise transferred to the identifying element 136 by an identifying element writing mechanism 140, as shown in step 236, prior to, simultaneous with, or subsequent to its securement to the bale 126. Further, as discussed, one or both of the calibration information and the evaluation information may be stored on a physical identifying element 136, in which one or both of the calibration information and the evaluation information may be electronically written or otherwise transferred to the physical identifying element 136 by the identifying element writing mechanism 140, as shown in step 238, such that this information and/or information can be subsequently directly read from the physical identifying element 136 using, e.g., an identifying element reading device 142.

The method 220 may include additional details discussed elsewhere herein, including those discussed above in describing the implemented system 120.

Additionally or alternatively, some embodiments may evaluate individual subunits of plant material incorporated into a bale and, based thereon, assign weighted average evaluation information to the overall bale. Under certain circumstances (e.g., during a headland turn) the NIR sensor may be exposed to a single flake, charge, or other subunit of a bale for thirty seconds or more, and when the bale is exiting the chamber the NIR sensor may be exposed to the last few subunits for only one or two seconds. By averaging the scanned spectra and/or property values for all or some of the subunits, the results can be equally weighted in the overall evaluation information for the bale.

For example, for crops of generally lower quality and yield, a baler traveling at a constant speed may take longer to fill its pre-compression chamber resulting in longer time periods between subunits. As a result, a time-based overall RFV and overall value may be one hundred twenty-two (122) and $130, while a position-based overall RFV and overall value may be one hundred fifty-five (155) and $160. For another example, the edges of fields often show reduced quality due to increased equipment traffic, so RFV scores during headland turns are often lower. As a result, a time-based overall RFV and overall value may be one hundred forty-three (143) and $160, while a position-based overall RFV and overall value may be one hundred ninety-one (191) and 225.

Thus, given a plurality of scanned spectra and/or property values for an individual bale, embodiments may weight each such spectra and/or value based on the amount of time the NIR sensor is exposed to the respective subunit of the bale, and then determines and assigns average scanned spectra and/or property values to the overall bale. In a field in which the subunits are largely homogenous in quality, the average property values may be substantially similar to each of the plurality of values, while in a field in which the subunits are of largely differing quality values, the average quality values may be significantly different from one or more of the individual values.

Figure 4:
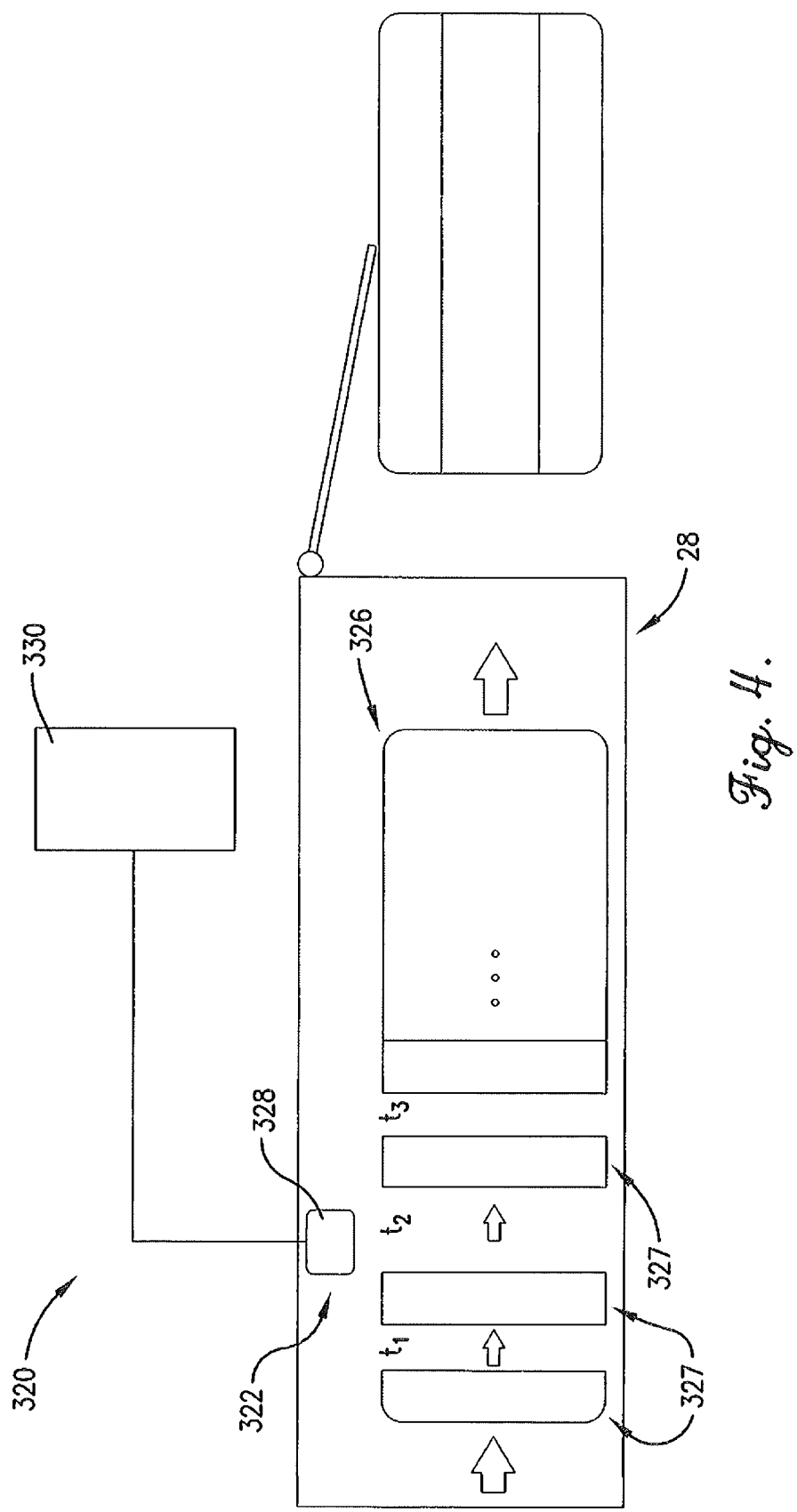
FIG. 4 is a high-level block diagram of an embodiment of a system for evaluating individual subunits of material incorporated in a bale and, based thereon, assigning a weighted average quality value to the overall bale.

Referring also to FIG. 4, an embodiment of a system 320 is shown for evaluating individual subunits of material incorporated into a bale and, based thereon, assigning a weighted average quality value to the overall bale. The system 320 is shown incorporated into an example operating environment. The system 320 may comprise some or all of the baler machine 20 and an NIR testing system 322, which may function in accordance with the method 420 described below. As discussed, the baler 20 may be configured to receive plant material and to compress, shape, and secure the plant material into a plurality of bales 326. More specifically, the baler 20 may be configured to receive a plurality of subunits 327 (also referred to as charges or flakes) of the material, and to aggregate, shape, and secure the plurality of subunits into individual bales 326. In one implementation, the baler 20 may be otherwise substantially conventional in design, construction, and operation.

The NIR testing system 322 may be configured to emit near-infrared radiation and receive a reflected response from the plant material in each subunit of two or more subunits of the plurality of subunits 327 and to analyze the reflected response and generate evaluation information reflecting one or more properties of the plant material in each subunit of the two or more subunits. This process may be performed for all or some of the bales (e.g., one of every five or fewer bales, or one of every ten or fewer bales).

In one implementation, the NIR testing system 322 may include one or more NIR sensors 328 and a computer 330. The NIR sensor 328 may be mounted in or on or otherwise incorporated into the baling chamber 28 or other area of the baler 20, and may be configured to receive, filter, and convert to a voltage or current the near-infrared radiation emitted by the plant material in each subunit of the two or more subunits of the bale 326, and transmit the voltage or current to the computer 330. The computer 330 may be located on or remotely from the baler 20, and may be configured to receive the voltage or current transmitted by the NIR sensor 328 and analyze the voltage or current to determine the properties of each subunit of the two or more subunits and generate the evaluation information. The computer 330 may be further configured to combine the evaluation information of the plant material in each subunit of the two or more subunits to produce one or more overall property values for the individual bale 326, assign the one or more overall property values to the individual bale 326, and save the one or more overall property values in a database. As discussed, combining the subunit evaluation information may include assigning an, e.g., time-based, position-based, or size-based weight to each such subunit evaluation information and then averaging the two or more sets of subunit evaluation information to arrive at the overall evaluation information for the bale 326. In one implementation, the evaluation information may include one or more of a protein content, a fiber content, nitrate content, ash content, a moisture content, and a relative feed value for the plant material in the bale 326.

The system 320 may include additional details discussed elsewhere herein, including those discussed below in describing the operating method 420.

Figure 5:
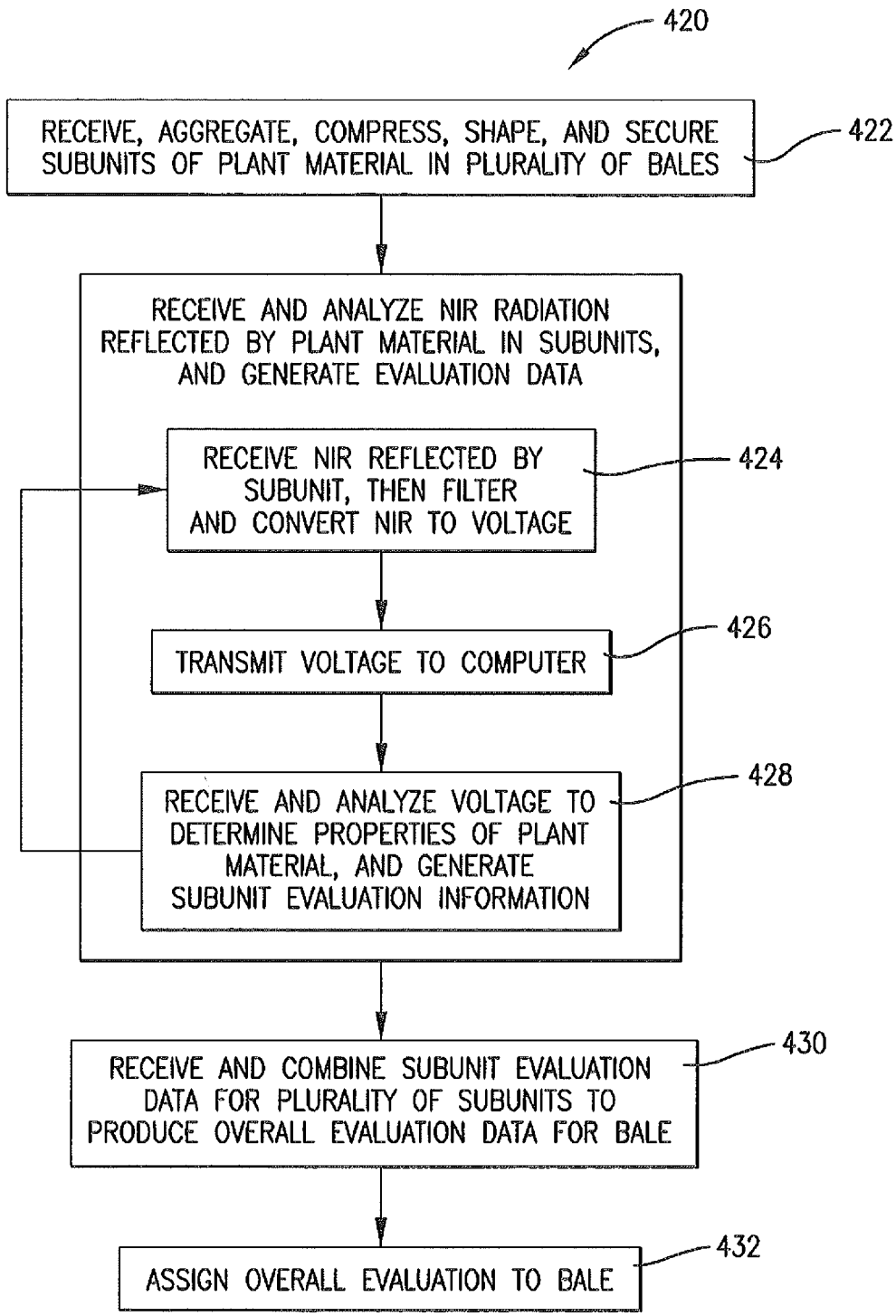
FIG. 5 is a flowchart of steps in an embodiment of a method for evaluating individual subunits of material incorporated in a bale and, based thereon, assigning a weighted average quality value to the overall bale.

Referring also to FIG. 5, an embodiment of a method 420 is shown for evaluating individual subunits of material incorporated in a bale and, based thereon, assigning a weighted average quality value to the overall bale. The method 420 may refer to an example operating environment. The method 420 may comprise some or all of the following steps, which may be implemented by components of the system 320 described above. As discussed, a plurality of subunits 327 (also referred to as charges or flakes) of plant material may be received, aggregated, compressed, shaped, and secured by a baler machine 20 into a plurality of bales 126, as shown in step 422.

Near-infrared radiation emitted by an NIR testing system 322 and reflected by the plant material in each subunit of two or more subunits of the plurality of subunits 327 may be received, filtered, and converted to a voltage or current by an NIR sensor 328 component of the NIR testing system 322, as shown in step 424, and the voltage or current may be transmitted to a computer 330 component of the NIR testing system 322, as shown in step 426. In various implementations, the NIR sensor 328 may be mounted in or on or otherwise incorporated into a baling chamber 28 or other area of the baler 20, and the computer 330 may be located on or remotely from the baler 20. In various implementations, one of every five or fewer bales may be subject to such testing, or one of every ten or fewer bales may be subject to such testing.

The voltage or current transmitted by the NIR sensor 328 may be received and analyzed by the computer 330 to determine the properties of the plant material and generate evaluation information reflecting one or more properties of the plant material in each subunit of the two or more subunits, as shown in step 428. The evaluation information of the plant material in each subunit of the two or more subunits may be combined by the computer 330 to produce one or more overall property values for the bale 326, as shown in step 430, and assign the one or more overall property values to the bale 326 as shown in step 432, and save the one or more overall property values in a database. As discussed, combining the subunit evaluation information may include assigning a weight (e.g., time-based, position-based, size-based) to each such subunit evaluation information and then averaging the two or more sets of subunit evaluation information to arrive at the overall evaluation information for the bale 326. In one implementation, the subunit evaluation information and the overall evaluation information may include one or more of a protein content, a fiber content, a nitrate content, an ash content, a moisture content, and a relative feed value for the plant material in the bale 326.

The method 420 may include additional details discussed elsewhere herein, including those discussed above in describing the implemented system 320.

Additionally or alternatively, embodiments may prepare a sample area of a bale in order to more accurately evaluate the material incorporated into the bale. More specifically, embodiments may prepare a portion of the surface of the bale by cutting, mixing, and then re-compressing the plant material so as to present a more homogeneous and representative sample to the NIR sensor. Embodiments may allow the NIR sensor to, in effect, scan to a greater depth of approximately twenty (20) millimeters.

Figure 6:
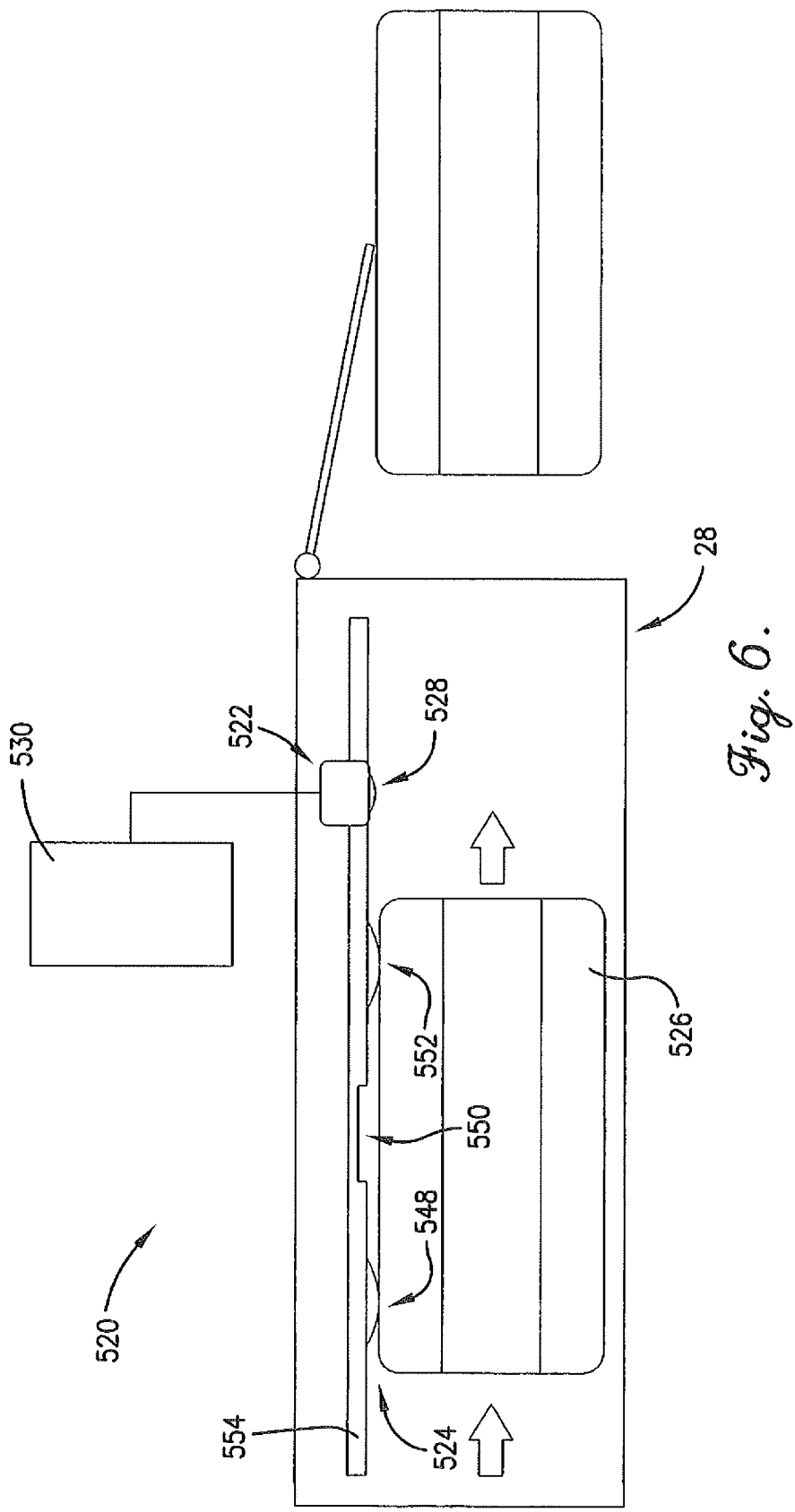
FIG. 6 is a high-level block diagram of an embodiment of a system for preparing a sample area of a bale in order to more accurately evaluate the material incorporated into the bale.
Figure 7:
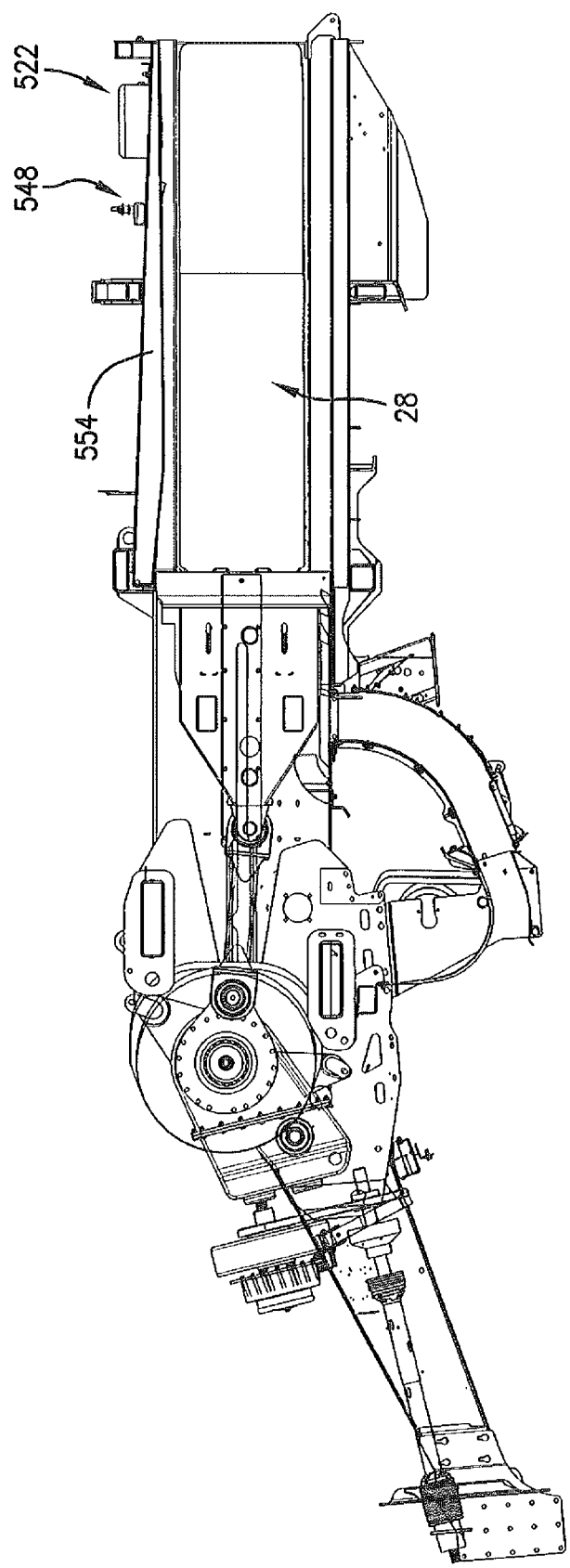
FIG. 7 is a fragmentary side elevation view of a compression chamber component of the baler machine of FIG. 1 showing various components of the system of FIG. 6.
Figure 8:
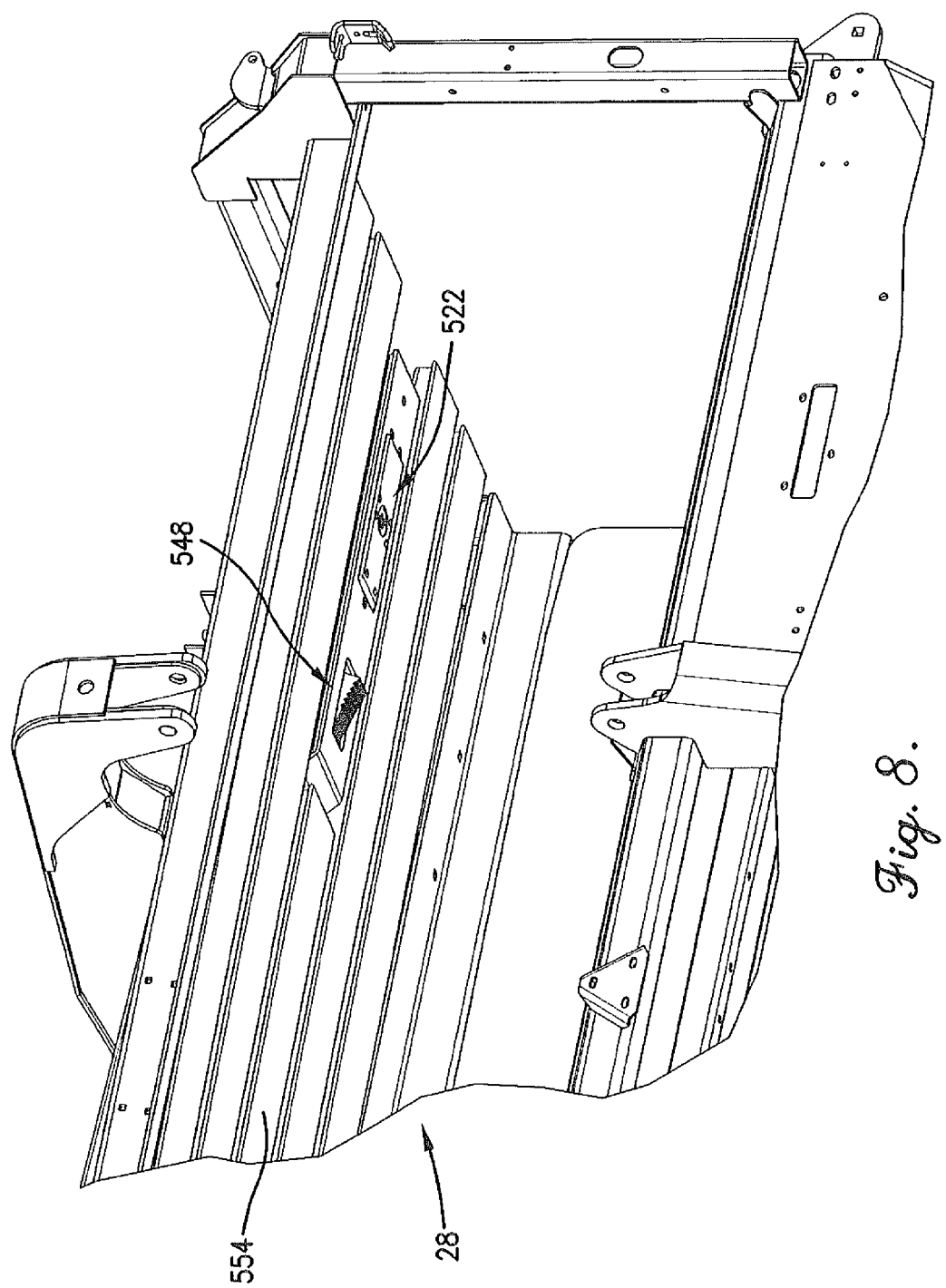
FIG. 8 is a fragmentary side elevation view of the various components of FIG. 7.

Referring also to FIGS. 6-8, an embodiment of a system 520 is shown for preparing a sample area of a bale in order to more accurately evaluate the material incorporated into the bale. The system 520 is shown incorporated into an example operating environment. The system 520 may comprise some or all of the baler machine 20, an NIR testing system 522, and a sample preparation mechanism 524, which may function in accordance with the method 620 described below. As discussed, the baler machine 20 may be configured to receive plant material and to compress, shape, and secure the plant material into a plurality of bales 526. In one implementation, the baler 20 may be otherwise substantially conventional in design, construction, and operation.

The NIR testing system 522 may be configured to emit near-infrared radiation and receive a reflected response from the plant material in all or some (e.g., one of every five or fewer bales, or one of every ten or fewer bales) of the bales, analyze the reflected response, and generate evaluation information reflecting one or more properties of the plant material in each analyzed bale, and may be associated with calibration information which is relevant to the accuracy of the evaluation information. In one implementation, the NIR testing system 522 may include one or more NIR sensors 528 and a computer 530. The NIR sensor 528 may be mounted in or on or otherwise incorporated into the baling chamber 28 or other area of the baler 20, and may be configured to receive, filter, and convert to a voltage or current the reflected response received from the plant material in each bale 526, and transmit the voltage or current to the computer 530. The computer 530 may be located on or remotely from the baler 20, and may be configured to receive the voltage or current transmitted by the NIR sensor 528 and analyze the voltage or current to determine the properties of each bale 526 and generate the evaluation information. In one implementation, the evaluation information may include one or more of a protein content, a fiber content, a nitrate content, an ash content, a moisture content, and a relative feed value for the plant material in the bale 526.

The sample preparation mechanism 524 may be configured to prepare a sample area 546 of the bale 526 which is subsequently exposed to the NIR sensor 528. As such, the sample preparation mechanism 524 may be located ahead (i.e., upstream) of the NIR sensor 528 in the baling chamber 28. The sample preparation mechanism 524 may include a cutter mechanism 548, a mixer mechanism 550, and a compression mechanism 552. In various implementations, the cutter, mixer, and/or compression mechanisms 548, 550, 552 may be one or more physically or functionally distinct or combined components/functionalities. For example, the cutter mechanism 548 and the mixer mechanism 550 may be two separate component or a single component which physically or functionally combines both mechanisms.

The cutter mechanism 548 may be configured to cut and/or grind a portion of the plant material (which consists of leaves and stems) in the sample area 546 of the bale 526 into similarly-sized particles of the plant material. In one implementation, the cutter mechanism 548 may include one or more spring-loaded serrated knives mounted in a fixed location (with the knives being otherwise shiftable against the bias of the spring) position such that sample area 548 moves against and is cut by the one or more spring-loaded serrated knives. In other implementations, the cutting/grinding element may be an auger, a grinder, or powered knives configured to produce substantially the same effect. The mixer mechanism 550 may be configured to mix the similarly-sized particles of the portion of the plant material into a homogenous aggregate of the portion of the plant material. The compression mechanism 552 may be configured to compress the homogenous aggregate of the portion of the plant material back into the bale 526 to provide a generally smooth surface for the NIR sensor 528 to scan. In one embodiment, the gutting/grinding element may include a rotary blade and stripper configured at a slight angle. It has been found that a slight blade angle accomplishes the mixing without any additional elements.

In one or more implementations, the cutter mechanism 548 may be positioned in the baling chamber 28 so as to cut and/or grind a portion of the plant material in the individual bale 526 without damaging a binding material which secures the baled plant material together. The baling chamber 28 may include a center rail structure 554, and the mixer mechanism 550 may be a relief feature on the center rail structure 554 which allows the cut and/or ground plant material to expand and mix. The relief feature may be further configured to allow any plant material falling from the cutter mechanism 548 to be gathered and mixed. The compression mechanism 552 may be a projecting feature on the center rail structure 554 which physically pushes against the surface of the bale 526 to compress the homogenous aggregate of the portion of the plant material so as to present a substantially flattened surface to the NIR sensor 528. The NIR sensor 528 may be mounted on the center rail 554 so as to cause the sensor lens to exert a pressure against the surface of the bale 526. Additionally or alternatively, the NIR sensor 528 may be located on a floating assembly mounted to the center rail 554 and configured to allow for controlling the pressure exerted against the surface of the bale 526.

The system 120 may include additional details discussed elsewhere herein, including those discussed below in describing the operating method 220.

Figure 9:
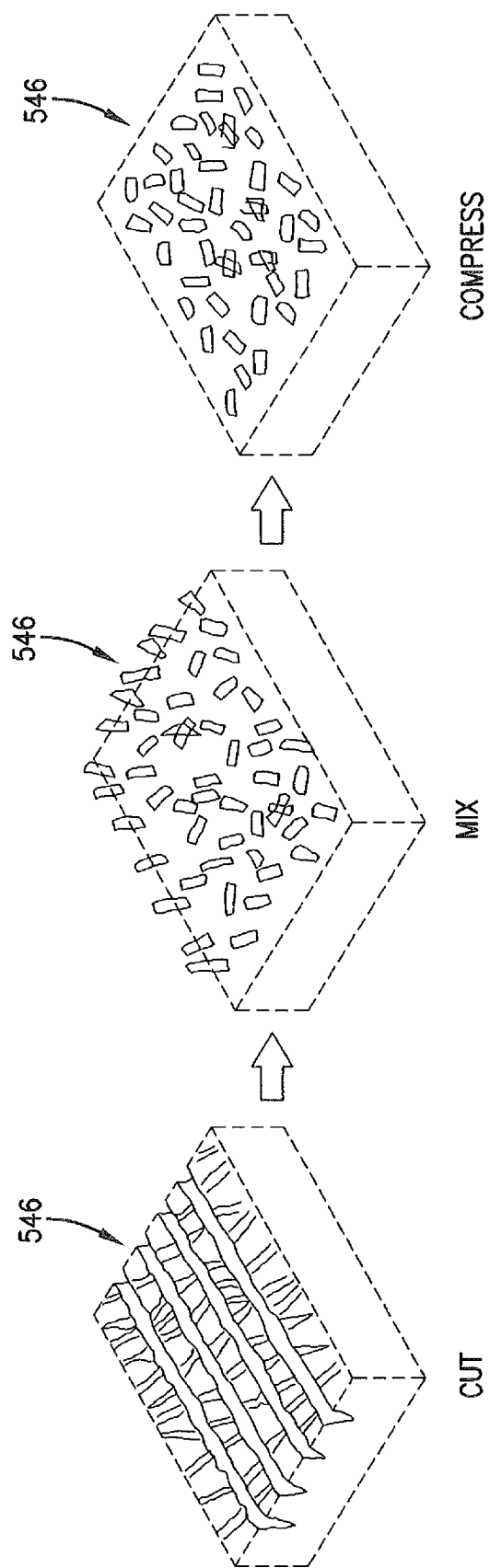
FIG. 9 is a progression of fragmentary cross-sectional isometric views showing the operations of the system of FIG. 6 on the sample area of the bale.
Figure 10:
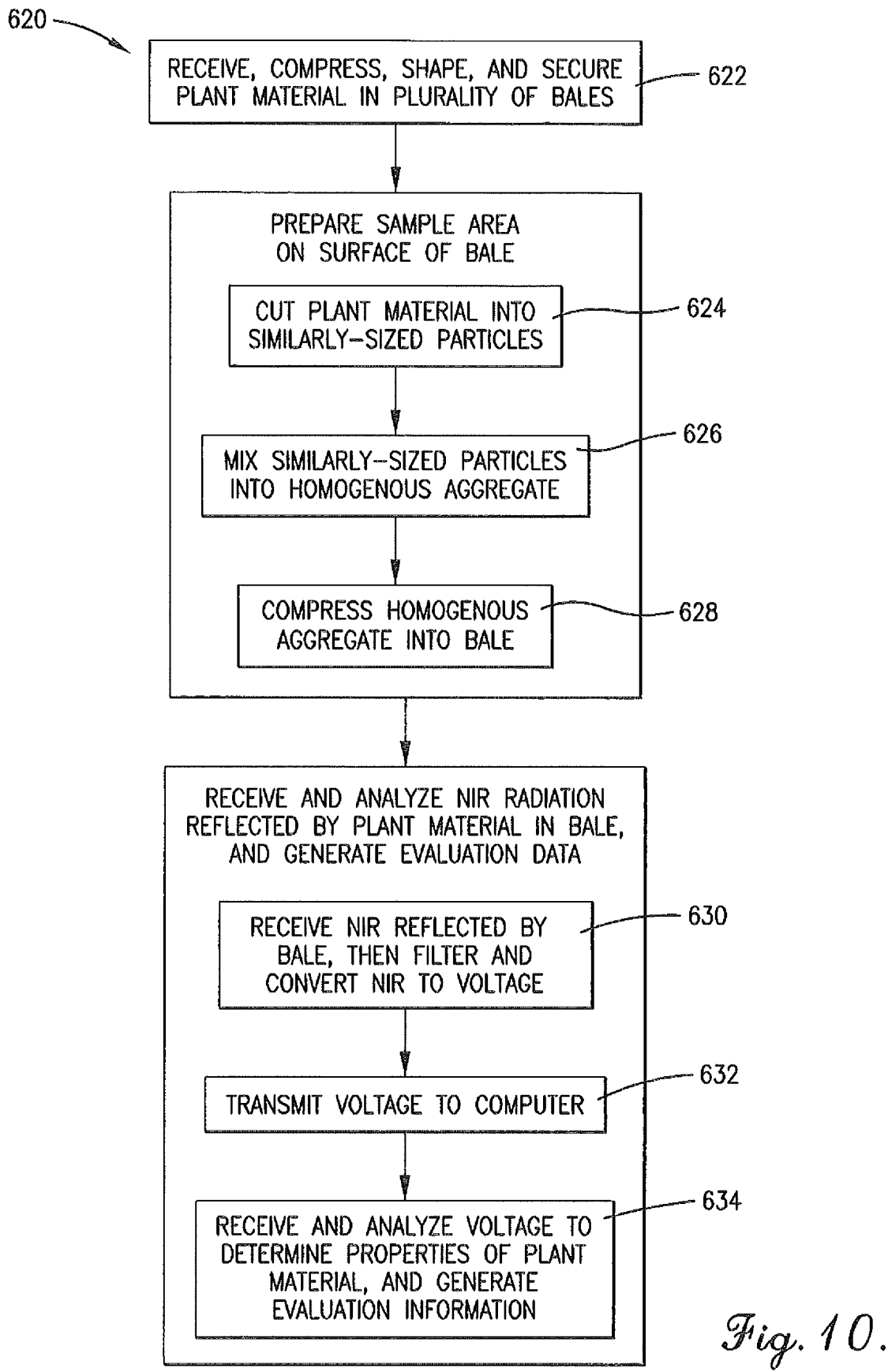
FIG. 10 is a flowchart of steps in an embodiment of a method for preparing a sample area of a bale in order to more accurately evaluate the material incorporated into the bale.

Referring also to FIG. 9, an embodiment of a method 620 is shown for preparing a sample area of a bale in order to more accurately evaluate the material incorporated into the bale. The method 620 may refer to an example operating environment. The method 620 may comprise some or all of the following steps, which may be implemented by components of the system 520 described above. As discussed, plant material may be received and shaped and secured by a baler machine 20 into a plurality of bales 526, as shown in step 622.

A sample area on a surface of some or all of the bales 526 may be prepared by a sample preparation mechanism 524. In various implementations, the sample preparation mechanism 524 may be mounted in or on or otherwise incorporated into the baling chamber 28 or other area of the baler 20. The sample preparation may include the following steps. A cutter mechanism 548 may cut and/or grind a portion of the plant material in the sample area 546 of the bale 526 into similarly-sized particles of the plant material, as shown in step 624. In one implementation, the cutter mechanism 548 may include one or more spring-loaded serrated knives mounted in a fixed position such that sample area 546 moves against and is cut by the one or more spring-loaded serrated knives. A mixer mechanism 550 may mix the similarly-sized particles of the portion of the plant material into a homogenous aggregate of the portion of the plant material, as shown in step 626. A compression mechanism 552 may compress the homogenous aggregate of the portion of the plant material back into the bale 526 to provide a generally smooth surface for an NIR sensor 528 to scan, as shown in step 630.

After the sample area 546 is prepared, near-infrared radiation is emitted and reflected by the plant material of the prepared sample area 546 in the bale 526, filtered, and converted to a voltage or current by the NIR sensor 528 component of an NIR testing system 522, as shown in step 630, and the voltage or current may be transmitted to a computer 530 component of the NIR testing system 522, as shown in step 632. In various implementations, the NIR sensor 528 may be mounted in or on or otherwise incorporated into the baling chamber 28 or other area of the baler 20, and the computer 530 may be located on or remotely from the baler 20. In one embodiment, every bale may be subject to such preparation and testing. In other implementations, one of every five or fewer bales may be subject to such preparation and testing, or one of every ten or fewer bales may be subject to such preparation and testing. Alternately, a field average may be applied on the task controller.

The voltage or current transmitted by the NIR sensor 528 may be received and analyzed by the computer 530 to determine the properties of the plant material and generate evaluation information, as shown in step 634. In one implementation, the evaluation information may include one or more of a protein content, a fiber content, nitrate content, ash content, a moisture content, and/or a relative feed value for the plant material in the bale 526.

The method 620 may include additional details discussed elsewhere herein, including those discussed above in describing the implemented system 520.

Figure 11:
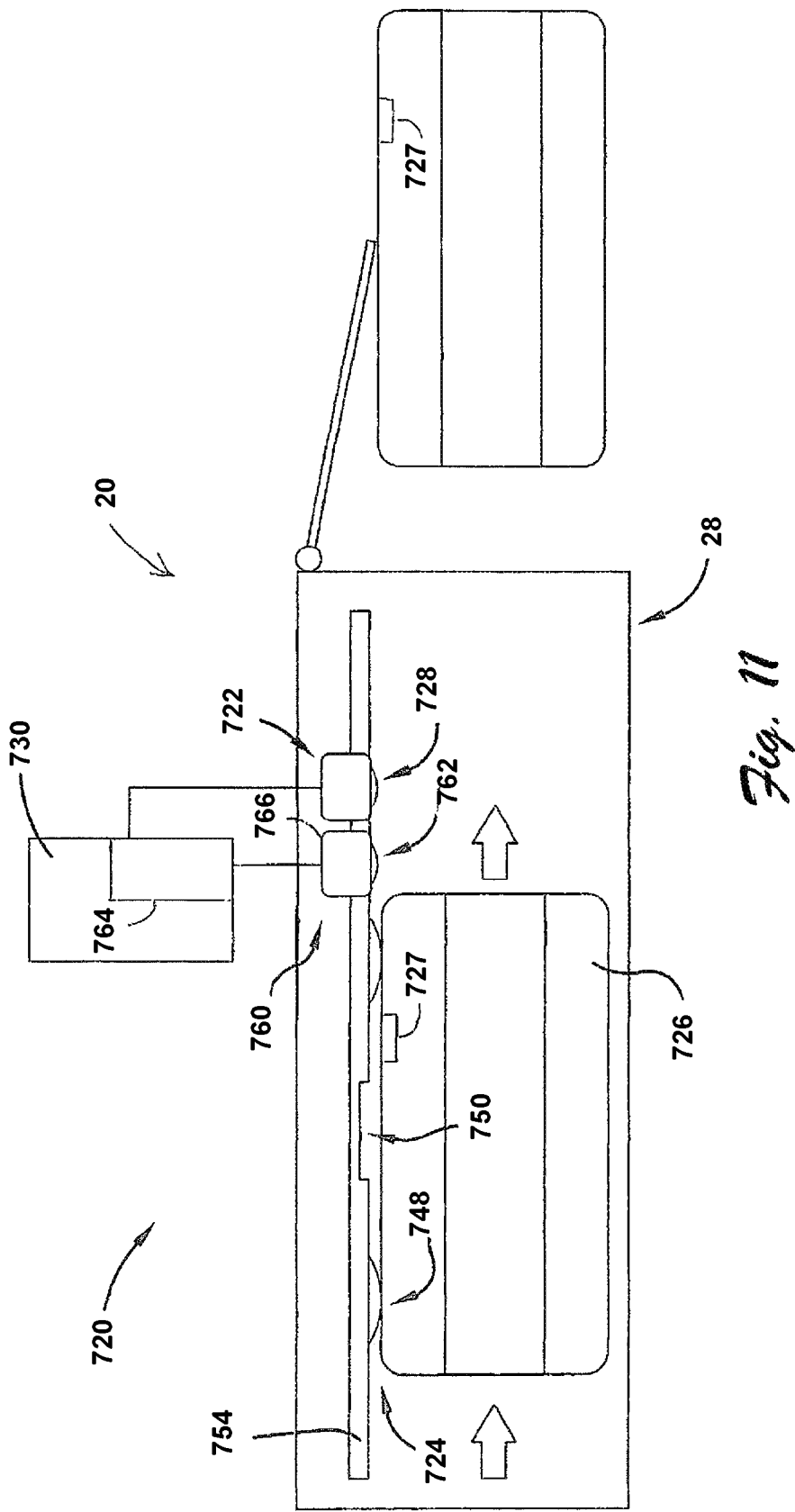
FIG. 11 is a fragmentary side elevation view of the various components of an alternate embodiment of the baler of FIG. 7.
Figure 12:
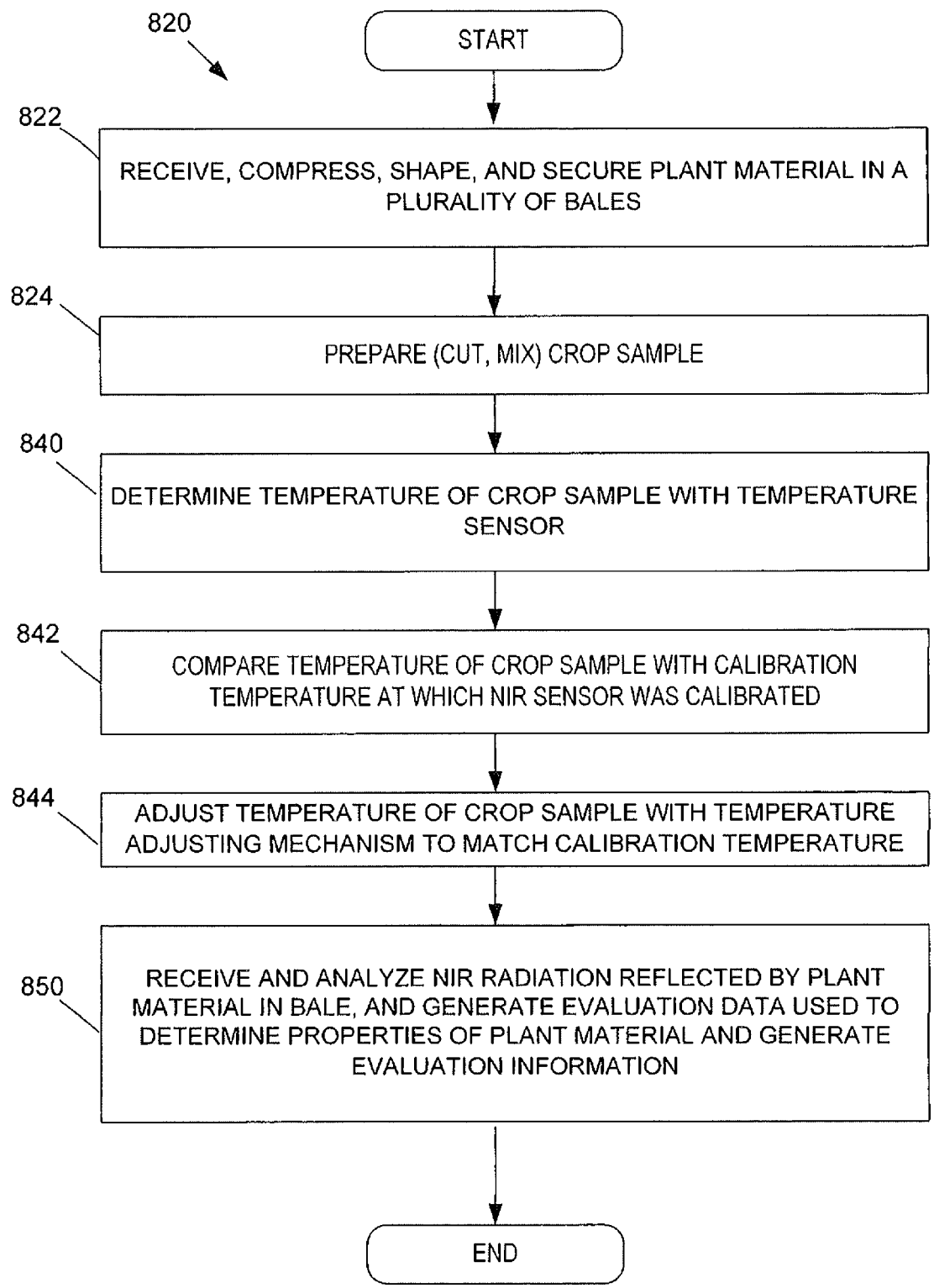
FIG. 12 is a flowchart of steps in an alternate embodiment of a method for preparing a sample area of a bale in order to more accurately evaluate the material incorporated into the bale.

FIGS. 11 and 12 show another embodiment of a system 720 having an NIR testing system 722 for preparing and testing a sample area of a bale. The system 720 is shown incorporated into an example operating environment. The system 720 may comprise some or all of the baler machine 20 and a sample preparation mechanism 724, as described above. As discussed, the baler machine 20 may be configured to receive plant material and to compress, shape, and secure the plant material into a plurality of bales 726. In one implementation, the baler 20 may be otherwise substantially conventional in design, construction, and operation.

The sample preparation mechanism 724 may be configured to prepare a crop sample 727 in the sample area of the bale 726 which is subsequently exposed to an NIR sensor 728 and includes a cutter mechanism 748, a mixer mechanism 750, and a compression mechanism 752 substantially similar to as described above. In one embodiment, the crop sample 727 is removed from the material of the bale 726 after the bale has been formed. However, it is understood that the crop sample 727 may be taken from the stream in the feeding system of the baler 20 without departing from the scope of the invention.

Also as discussed above, the NIR sensor 728 may be configured to emit near-infrared radiation and receive a reflected response from the plant material in the crop sample 727 of all or some (e.g., one of every five or fewer bales, or one of every ten or fewer bales) of the bales, analyze the reflected response, and generate evaluation information reflecting one or more properties of the plant material in each analyzed bale, and may be associated with calibration information which is relevant to the accuracy of the evaluation information.

The system 720 also contains a temperature compensation system 760 in order to more accurately evaluate the material incorporated into the bale 726. The temperature compensation system 760 contains at least one temperature sensor 762 configured to sense the temperature of the plant material in the crop sample 727 of the bale 726. In one embodiment, the crop sample 727 is remove from the main material flow of the baler 20, prepared to a desired particle size by the cutter mechanism 748 and a mixer mechanism 750 consistent with a particle size of the crop used when performing a calibration process of the NIR sensor 728. The temperature sensor 762 senses the crop temperature in the prepared crop sample 727 and the temperature compensation system 760 compensates for any temperature difference between the actual temperature of the crop sample 727 and the temperature of the sample used during a calibration process of the NIR sensor 728. In one embodiment, the temperature sensor 762 is a non-contact IR based temperature sensor, but the temperature sensor 762 could also be based on numerous other known technologies without departing from the scope of the invention. Multiple Temperature sensors 762 may be used and the average of the temperatures recorded by the multiple sensors may be used for the temperature of the crop sample 727. The multiple temperature sensors 762 may be positioned in different locations of the sample preparation mechanism 724 such as, for example, one before the cutter mechanism 748 and one after the mixer mechanism 750.

In one embodiment, the temperature compensation system 760 contains a controller 764, perhaps as part of computer 730, and a temperature alteration mechanism 766 used to alter the crop temperature of the crop sample 727 to match the calibration temperature. The controller 764 receives a temperature signal corresponding to the temperature of the crop sample 727 and controls the temperature alteration mechanism 766 to heat or cool the crop sample 727 as necessary to make the temperature of the crop sample 727 such that it is within a desired band, for example, plus or minus 10 degrees Fahrenheit, of the calibration temperature. For example, in one embodiment a calibration temperature of 70 degrees F. is used. If the temperature sensor 762 senses that the temperature of the crop sample 727 is 40 degrees F. (such as might be the case if baling crop material in cold weather), the controller 764 has the temperature alteration mechanism 766 heat the crop sample 727 to a temperature within a desired band around 70 degrees F. On the other hand, if the temperature sensor 762 senses that the temperature of the crop sample is 90 degrees F., the controller 764 has the temperature alteration mechanism 766 cool the crop sample 727 to a temperature within the desired band around 70 degrees F. The temperature alteration mechanism may be any known Peltier device or thermoelectric cooler (TEC) that uses the Peltier effect to create a heat flux which transfers heat from one side of the device to the other depending on the direction of an applied current, or other suitable temperature alteration mechanism using sound engineering judgment. After the crop sample 727 has been sensed by the temperature sensor 762 and the NIR sensor 728, it may either be left as part of the bale, reintroduced to the feeding system of the baler 20, or discarded either to the surface bale 726, to the field, or some collection device so the sample could be used for comparison at a later point.

The system 720 may include additional details discussed elsewhere herein, including those discussed below in describing the operating method 820. Referring also to FIG. 12, an embodiment of a method 820 is shown for preparing a sample area of a bale in order to more accurately evaluate the material incorporated into the bale. The method 820 may refer to an example operating environment. The method 820 may comprise some or all of the following steps, which may be implemented by components of the system 720 described above. As discussed, plant material may be received and shaped and secured by a baler machine 20 into a plurality of bales 726, as shown in step 822.

A crop sample 727 is prepared as shown in step 824. After the crop sample 727 is prepared, the temperature of crop sample 727 is determined with temperature sensor 762, as shown in step 840. The temperature of crop sample 727 is compared with the calibration temperature at which the NIR sensor 728 was calibrated, as shown in step 842. The temperature of crop sample 727 is adjusted with the temperature adjusting mechanism 766 to match the calibration temperature of the NIR sensor 728, as shown in step 844. Near-infrared radiation is emitted and reflected by the plant material of the prepared sample 727, filtered, and converted to a voltage or current by the NIR sensor 728 of the NIR testing system 722, as shown in step 850, In various implementations, the NIR sensor 728 may be mounted in or on or otherwise incorporated into the baling chamber 28 or other area of the baler 20, and the computer 730 may be located on or remotely from the baler 20. In various implementations, every bale may be subject to such preparation and testing, or one of every five or fewer bales may be subject to such preparation and testing, or one of every ten or fewer bales may be subject to such preparation and testing. The voltage or current transmitted by the NIR sensor 728 may be received and analyzed by the computer 730 to determine the properties of the plant material and generate evaluation information. In one implementation, the evaluation information may include one or more of a protein content, a fiber content, nitrate content, ash content, a moisture content, and/or a relative feed value for the plant material in the bale 726.

Figure 13:
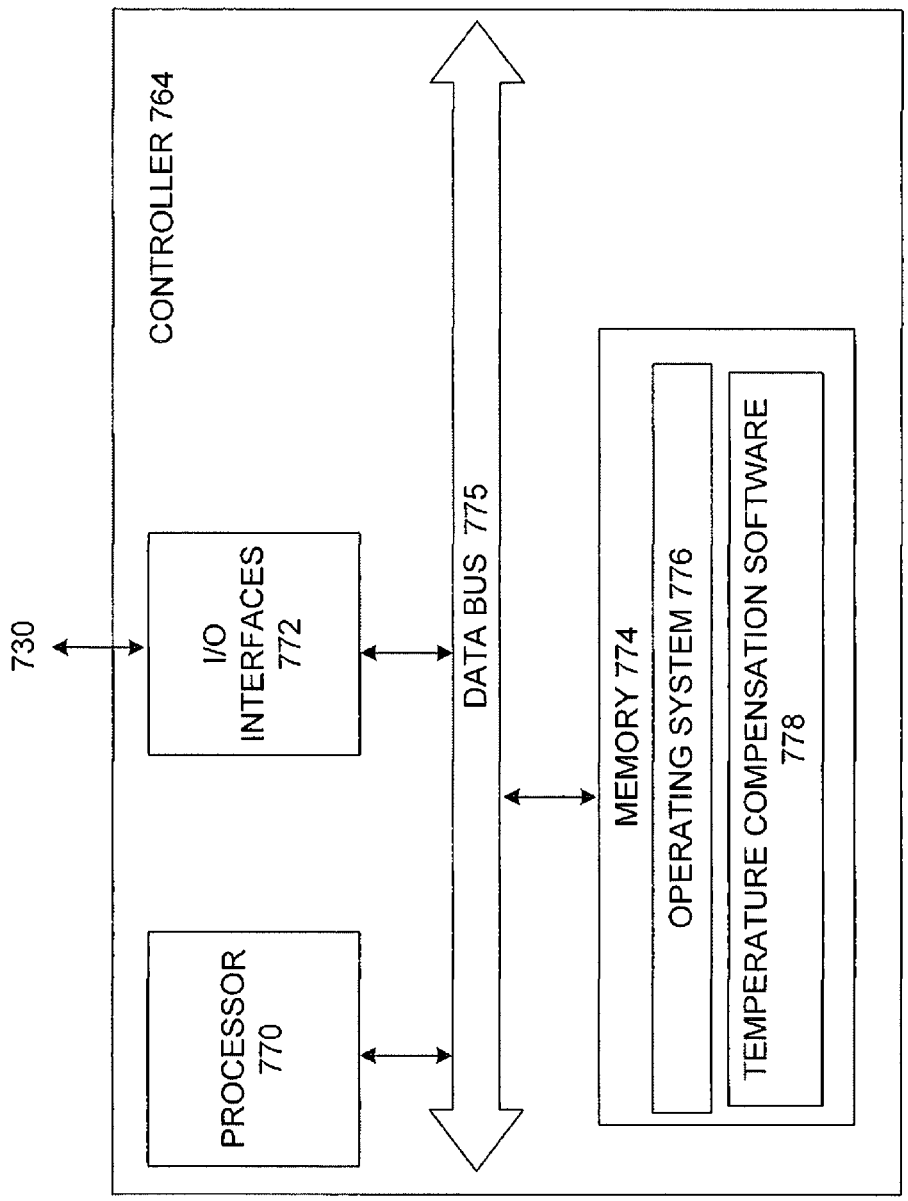
FIG. 13 is a block diagram of an embodiment of an example controller used in the system of FIG. 11.
Figure 14:
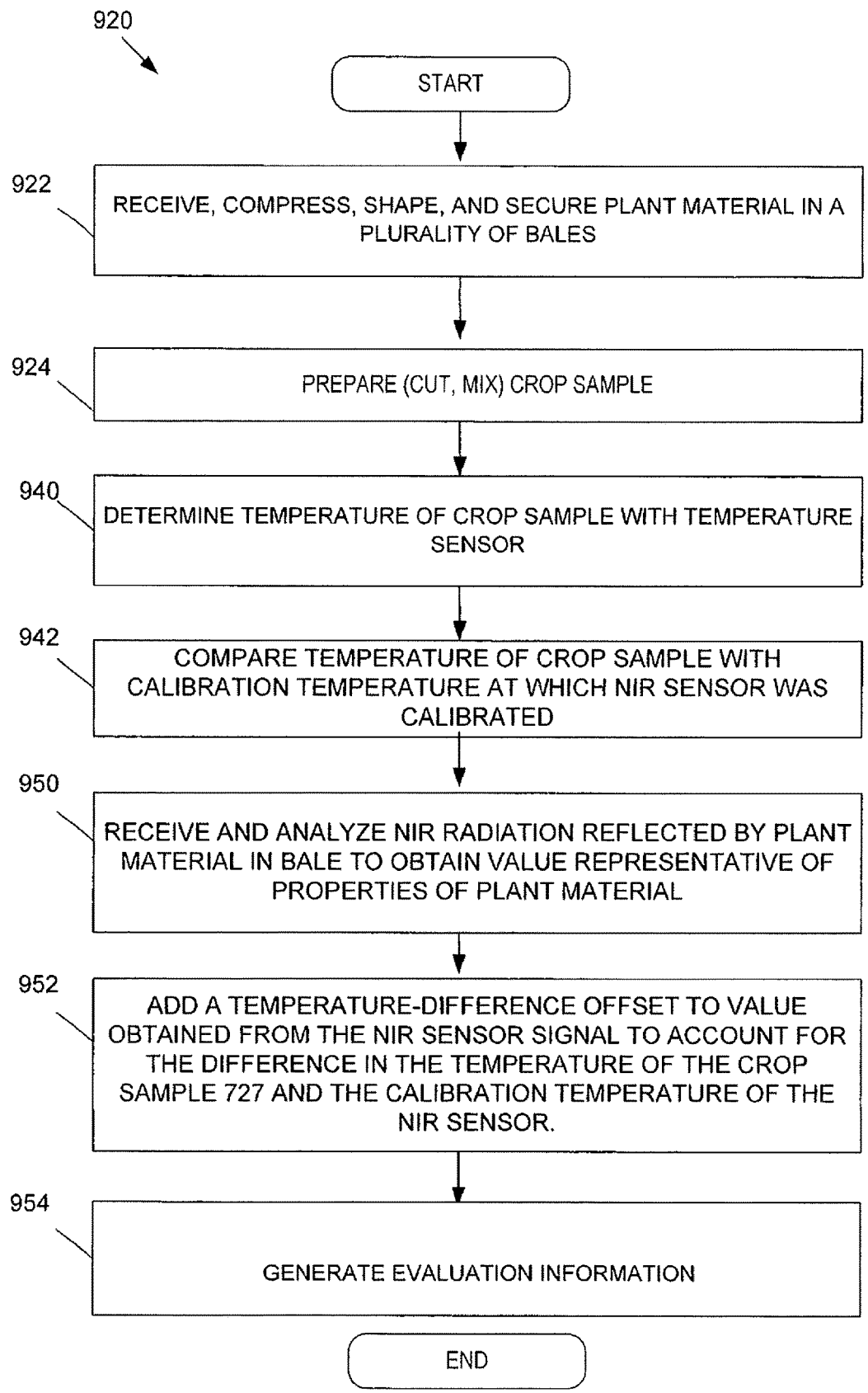
FIG. 14 is a flowchart of steps in an alternate embodiment of a method for preparing a sample area of a bale in order to more accurately evaluate the material incorporated into the bale.

Turning now to FIGS. 11 and 13-14, another embodiment of the system 720 having an NIR testing system 722 and sample preparation mechanism 724 for preparing and testing the crop sample 727 in the sample area of the bale 726 using the temperature compensation system 760 in order to more accurately evaluate the material incorporated into the bale 726 is shown. The temperature compensation system 760 contains at least one temperature sensor 762 configured to sense the temperature of the plant material in the crop sample 727 of the bale 726. The crop sample 727 is desirably removed from the main material flow of the baler 20 and prepared to a desired particle size by the cutter mechanism 748 and the mixer mechanism 750 consistent with a particle size of the crop used when performing a calibration process of the NIR sensor 728. The temperature sensor 762 senses the crop temperature in the prepared crop sample 727 and the temperature compensation system 760 adds a temperature offset to the measurements generated from the NIR sensor 728 to compensate for differences in the measurements introduced as a result of the temperature difference between the actual temperature of the crop sample 727 and the temperature of the sample that was used during the calibration process of the NIR sensor 728. In one embodiment, the offset is experimentally generated and obtained using suitable algorithms or lookup tables. In one embodiment, the NIR sensor 728 is used to predict constituents such as fiber or protein of the crop sample 727, and the controller 764 corrects the uncompensated results by applying the offset to account for the actual crop temperature being different than the calibration temperature. In one case, the offset could be a simple linear offset for all values. In other cases, certain constituents such as fiber tend to vary the slop of the offset with varying levels. For instance a forage with a score of 200 RFV may have a significantly different offset value than a forage with an RFV of 120 for a given temperature. In this case, the instrument prediction obtained with the NIR sensor 728 and the crop sample temperature are used to apply a specific offset for the value range of the instrument prediction. Accordingly, the controller 764 receives a signal from the temperature sensor 762 corresponding to the actual temperature of the crop sample 727 and a signal from the NIR sensor 728 corresponding the properties of the crop sample 727 to be measured and applies the offset to obtain compensated NIR measured constituents before presenting the values to the operator or assigning them to an individual bale 726. It has been found that that attributes have a linear trend, and the offsets may be a function of the sample container lens distorting the data. Desirably, temperature offsets are applied to the final calibration predictions being reported to the baler controller, but it is also possible to transform the raw spectra before the calibration is used to generate a prediction.

FIG. 13 further illustrates an example embodiment of the controller 764. One having ordinary skill in the art should appreciate in the context of the present disclosure that the example controller 764 is merely illustrative, and that some embodiments of controllers may comprise fewer or additional components, and/or some of the functionality associated with the various components depicted in FIG. 14 may be combined, or further distributed among additional modules, in some embodiments. It should be appreciated that, though described in the context of residing in the baler 20 (FIG. 1), in some embodiments, the controller 764, or all or a portion of its corresponding functionality, may be implemented in a computing device or system located external to the baler 20. Referring to FIG. 14, with continued reference to FIG. 11, the controller 764 or electronic control unit (ECU) is depicted in this example as a computer, but may be embodied as a programmable logic controller (PLC), field programmable gate array (FPGA), application specific integrated circuit (ASIC), among other devices. It should be appreciated that certain well-known components of computers are omitted here to avoid obfuscating relevant features of the controller 764. In one embodiment, the controller 764 comprises one or more processors (also referred to herein as processor units or processing units), such as processor 770, input/output (I/O) interface(s) 772, and memory 774, all coupled to one or more data busses, such as data bus 775. The memory 774 may include any one or a combination of volatile memory elements (random-access memory RANI, such as DRAM, and SRAM, etc.) and nonvolatile memory elements (e.g., ROM, Flash, hard drive, EPROM, EEPROM, CDROM, etc.). The memory 774 may store a native operating system, one or more native applications, emulation systems, or emulated applications for any of a variety of operating systems and/or emulated hardware platforms, emulated operating systems, etc.

In the embodiment depicted in FIG. 13, the memory 774 comprises an operating system 776 and temperature compensation software 778. It should be appreciated that in some embodiments, additional or fewer software modules (e.g., combined functionality) may be deployed in the memory 772 or additional memory. In some embodiments, a separate storage device may be coupled to the data bus 775, such as a persistent memory (e.g., optical, magnetic, and/or semiconductor memory and associated drives).

The temperature compensation software 778 receives sensor input from one or more temperature sensors 762 and input from the NIR sensor 728. The temperature compensation software 778 processes the plural inputs to derive a compensated value or values to communicate to the adjustment mechanisms 86. The temperature compensation software 778 may compare the values received from the sensor input in a look up table (e.g., stored in memory 774) that associates the parameters to a respective adjustment value. In some embodiments, the parameters are used in a formula that the temperature compensation software 778 computes to derive the offset value. The offset value may be based on a moving average (or other statistical values) of prior sensor input (with the window of the moving average defined by a predetermined time and/or distance traveled by the baler 20, FIG. 1), or continually updated in finer increments of time (e.g., as sensor input is received) in some embodiments. Further, in some embodiments, adjustment values may be continuously variable values or rounded up or down (or interpolated) to fixed incremental values in some embodiments.

Execution of the temperature compensation software 778 may be implemented by the processor 770 under the management and/or control of the operating system 776. The processor 770 may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the controller 764.

When certain embodiments of the controller 764 are implemented at least in part with software (including firmware), as depicted in FIG. 13, it should be noted that the software can be stored on a variety of non-transitory computer-readable medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiment of the controller 764 are implemented at least in part with hardware, such functionality may be implemented with any or a combination of the following technologies, which are all well-known in the art: a discreet logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The system 720 may include additional details discussed elsewhere herein, including those discussed below in describing operating method 920. Referring also to FIG. 14, an embodiment of a method 920 is shown for preparing a sample area of a bale in order to more accurately evaluate the material incorporated into the bale. The method 920 may refer to an example operating environment. The method 920 may comprise some or all of the following steps, which may be implemented by components of the system 720 described above. As discussed, plant material may be received and shaped and secured by a baler machine 20 into a plurality of bales 726, as shown in step 922. A crop sample 727 is prepared as shown in step 924. After the crop sample 727 is prepared, the temperature of crop sample is determined with temperature sensor 762, as shown in step 940. The temperature of crop sample 727 is compared with the calibration temperature at which the NIR sensor 728 was calibrated, as shown in step 942. Near-infrared radiation is emitted and reflected by the plant material of the prepared sample 727, filtered, and converted to a voltage or current signal by the NIR sensor 728 of the NIR testing system 722 that is representative of evaluation information of the crop sample 727, as shown in step 950. A temperature-difference offset is added to results obtained from the NIR sensor signal to account for the difference in the temperature of the crop sample 727 and the calibration temperature of the NIR sensor 728, as shown at step 952. Temperature-compensated evaluation information is generated and presented to the operator, as shown at step 954. In various implementations, the NIR sensor 728 may be mounted in or on or otherwise incorporated into the baling chamber 28 or other area of the baler 20, and the computer 730 may be located on or remotely from the baler 20. In various implementations, one of every five or fewer bales may be subject to such preparation and testing, or one of every ten or fewer bales may be subject to such preparation and testing. The voltage or current transmitted by the NIR sensor 728 may be received and analyzed by the computer 730 to determine the properties of the plant material and generate evaluation information. In one implementation, the evaluation information may include one or more of a protein content, a fiber content, nitrate content, ash content, a moisture content, and/or a relative feed value for the plant material in the bale 726. The evaluation information could also include a serial number or other identifier for the temperature compensation software that could be applied to a bale identifier such as an RFID attached to the bale.

It will be appreciated that two or more of the above-described embodiments or particular details thereof may be combined as need or desired. For example, the embodiment in which individual subunits of a bale are tested and the results combined to create more accurate overall evaluation information for the bale may be combined with the embodiment in which an individual bale is tagged, to result in an embodiment in which the identifying element contains or the unique identifier can be used to find the more accurate overall evaluation information.

Although the invention has been described with reference to the one or more embodiments illustrated in the figures, it is understood that equivalents may be employed and substitutions made herein without departing from the scope of the invention as recited in the claims.

Having thus described one or more embodiments of the invention, what is claimed as new and desired to be protected by Letters Patent includes the following:

1. A system incorporated into a baler machine configured to receive a plant material, and to aggregate, compress, shape, and secure the plant material into a plurality of bales, the system comprising:
   a near-infrared testing system configured to receive near-infrared radiation reflected by the plant material in at least one bale of the plurality of bales and to analyze the near-infrared radiation and generate evaluation data reflecting one or more properties of the plant material in the at least one bale, wherein the near-infrared testing system is calibrated using a calibration sample at a calibration temperature;
   a temperature sensor configured to measure a sample temperature of a crop sample of the plant material;
   a computer configured to receive and combine the evaluation data of the plant material and a temperature-difference offset based on a temperature difference value to account for difference in the sample temperature of the crop sample and the calibration temperature to produce overall temperature-compensated evaluation data reflecting one or more overall property values for the bale, and assign the overall temperature-compensated evaluation data to the at least one bale of the plurality of bales.

2. The system of claim 1 wherein the temperature sensor is a non-contact infra-red (IR) based temperature sensor.

3. The system of claim 1 further comprising:
   a cutter mechanism configured to cut a portion of the plant material in the bale into similarly-sized particles of the plant material;
   a mixer mechanism configured to mix the similarly-sized particles of the portion of the plant material into a homogenous aggregate of the portion of the plant material; and
   a compression mechanism configured to compress the homogenous aggregate of the portion of the plant material into the bale.

4. The system of claim 3, wherein the cutter mechanism includes one or more rotary blades mounted such that bale moves against and is cut by the one or more rotary blades.

5. A method for sampling agricultural crop material formed into a bale comprising:
   calibrating a near-infrared testing system using a calibration sample having a calibration sample temperature;
   receiving, aggregating, shaping, and securing plant material into a bale with a baler machine;
   preparing a crop sample of the plant material of the bale
   measuring the temperature of the crop sample with a temperature sensor;
   comparing the temperature of the crop sample with the calibration sample temperature at which the near-infrared testing system was calibrated to obtain a temperature difference value;
   receiving and analyzing with the near-infrared testing system near-infrared radiation reflected by the plant material in the crop sample of the bale, and generating evaluation data reflecting one or more properties of the plant material in the bale;
   receiving and combining with a computer the evaluation data of the plant material and adding a temperature difference offset to account for difference in the temperature of the crop sample and the calibration sample temperature to produce overall temperature-compensated evaluation data reflecting one or more overall property values for the bale; and
   assigning with the computer the overall temperature compensated evaluation data to the bale.

6. The method of claim 5 wherein the evaluation data includes one or more of a protein content, a fiber content, nitrate content, ash content, a moisture content, and a relative feed value for the plant material in the bale.

* * * * *